(12) United States Patent
Cohen et al.

(10) Patent No.: US 11,432,755 B2
(45) Date of Patent: Sep. 6, 2022

(54) SYSTEMS AND METHODS FOR CLUSTERING WAVEFRONT SIGNALS IN ELECTROPHYSIOLOGICAL MAPS

(71) Applicant: Biosense Webster (Israel) Ltd., Yokneam (IL)

(72) Inventors: Assaf Cohen, Kiryat Bialik (IL); Fady Massarwi, Baka Al Gharbiyya (IL); Sigal Altman, Ramat Hashofet (IL); Gal Bar Zohar, Yokneam Moshava (IL); Leonid Zaides, Atlit (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 86 days.

(21) Appl. No.: 17/027,252

(22) Filed: Sep. 21, 2020

(65) Prior Publication Data

US 2022/0087560 A1  Mar. 24, 2022

(51) Int. Cl.
   *A61B 5/341* (2021.01)
   *A61B 5/00* (2006.01)
   *A61B 5/339* (2021.01)
   *G06K 9/62* (2022.01)

(52) U.S. Cl.
   CPC .............. *A61B 5/341* (2021.01); *A61B 5/339* (2021.01); *A61B 5/7235* (2013.01); *A61B 5/7275* (2013.01); *G06K 9/6218* (2013.01)

(58) Field of Classification Search
   CPC ....... A61B 5/341; A61B 5/339; A61B 5/7235; A61B 5/7275; G06K 9/6218
   See application file for complete search history.

(56) References Cited

U.S. PATENT DOCUMENTS

| | | | |
|---|---|---|---|
| 6,301,496 B1 * | 10/2001 | Reisfeld | A61B 5/341 600/407 |
| 10,282,888 B2 | 5/2019 | Zar | |
| 10,674,929 B2 | 6/2020 | Houben | |
| 2009/0163973 A1 | 6/2009 | Meyer | |
| 2013/0274582 A1 * | 10/2013 | Afonso | A61B 5/065 600/374 |
| 2015/0065836 A1 | 3/2015 | Thakur et al. | |

(Continued)

FOREIGN PATENT DOCUMENTS

| | | |
|---|---|---|
| EP | 3344124 A1 | 7/2018 |
| WO | 2017/040581 A1 | 3/2017 |

OTHER PUBLICATIONS

Extended European Search Report dated Feb. 7, 2022 for European Patent Application No. 21197691.5.

(Continued)

*Primary Examiner* — Catherine M Voorhees
(74) *Attorney, Agent, or Firm* — Volpe Koenig

(57) ABSTRACT

A system and method for clustering wavefront signals in an electrophysiological map of a cardiac tissue are provided. The system and method include receiving an electrophysiological map of the cardiac tissue, displaying propagation of the wavefront signals as a plurality of velocity vectors, discretizing the received electrophysiological map into a plurality of sections, clustering the velocity vectors into at least one group within each section based on predefined criteria, and generating a trend line representative of each group of clustered velocity vectors within each section in the electrophysiological map.

18 Claims, 6 Drawing Sheets

(56) References Cited

U.S. PATENT DOCUMENTS

| | | |
|---|---|---|
| 2017/0311834 A1 | 11/2017 | Thakur |
| 2018/0296111 A1 | 10/2018 | Deno et al. |
| 2019/0357793 A1* | 11/2019 | Ruppersberg .......... A61B 5/361 |
| 2021/0000369 A1* | 1/2021 | Luksic ................... A61B 34/20 |
| 2021/0038171 A1* | 2/2021 | Katz .................... A61B 5/7485 |
| 2022/0015682 A1* | 1/2022 | Spector ................. A61B 5/367 |

OTHER PUBLICATIONS

Rita Yassi et al, "The gastrointestinal electrical mapping suite (GEMS): software for analyzing and visualizing high-resolution (multi-electrode) recordings in spatiotemporal detail", BMC Gastroenterol 12, 60 (2012).

\* cited by examiner

500

510

SYSTEMS AND METHODS FOR CLUSTERING WAVEFRONT SIGNALS IN ELECTROPHYSIOLOGICAL MAPS

FIELD OF INVENTION

The present invention is related to systems, methods, apparatuses, and programs for clustering wavefront signals for simplification in electrophysiological maps.

BACKGROUND

Visualization of cardiac structures is critical for observing and diagnosing cardiac health and to perform certain cardiac procedures. For example, as a prerequisite to performing a cardiac procedure, an electrophysiological investigation is often performed to generate an electrophysiological (EP) cardiac map in which three-dimensional or 3D mapping data can be displayed on a monitor.

Various methods are known in the art for reconstructing a 3D EP map of a cardiac cavity or volume using the known position coordinates of a plurality of locations on the surface of the cavity or volume. An example of cardiac EP mapping requires a determination of the velocity and direction of propagation of electrical signals through the heart tissue. Abnormal propagation velocity, or vortical signal flow, may be diagnostic of locally diseased heart tissue that can be treated, for example, by ablation.

Typically, the velocity of propagation of cardiac signals is measured by sensing a wavefront signal at a plurality of electrodes in contact with the inner surface of a heart chamber. An example of a known method for measuring velocity propagation of cardiac signals utilizes measurements of local activation time (LAT) of heart tissue, relative to the cardiac cycle, at a plurality of sampled points on the inner surface of a chamber of the heart, using a device, such as a catheter, that senses electrical activity at a point of contact of the catheter tip with the inner surface of the chamber of the heart. These measurements of LAT can be displayed in an EP cardiac map as conduction velocity vectors and represented, for example, by arrows, at the measurement points, with the directions of the arrows representing the direction of propagation of the wavefront and the lengths of the arrows representing the velocity of propagation of the wavefront. These arrows provide a visual display of propagation velocity that enables a physician to identify the location of diseased cardiac tissue that should be treated.

Conventionally, the amount of graphical information, in the form of vectors or arrows, is significant and difficult to interpret, particularly for inexperienced physicians. It would be advantageous to a physician to be able to view an EP cardiac map displaying direction and velocity of propagation of wavefront signals in a simplified manner that reduces the volume of information presented by vectors in current EP mapping systems in order to make the wavefront information more easily comprehendible.

SUMMARY

Systems, methods, apparatuses, and programs for clustering wavefront signals for simplification in electrophysiological (EP) maps are disclosed herein.

In accordance with one an aspect, the subject matter disclosed herein relates to a method for clustering wavefront signals in an electrophysiological map of a cardiac tissue. The method comprises providing a processor configured to receive an electrophysiological map of the cardiac tissue, displaying propagation of the wavefront signals as a plurality of velocity vectors, discretizing the received electrophysiological map into a plurality of sections, clustering the velocity vectors into at least one group within each section based on predefined criteria, and generating a trend line representative of each group of clustered velocity vectors within each section in the electrophysiological map.

In accordance with another aspect, the subject matter disclosed herein relates to a system for clustering wavefront signals in an electrophysiological map of a cardiac tissue. The system comprises a processor comprising a memory configured to receive an electrophysiological map of the cardiac tissue displaying propagation of the wavefront signals as a plurality of velocity vectors, discretize the received electrophysiological map into a plurality of sections, cluster the velocity vectors into at least one group within each section based on predefined criteria, and generate a trend line representative of each group of clustered velocity vectors within each section in the electrophysiological map.

In accordance with yet another aspect, the subject matter disclosed herein relates to a computer readable recording medium storing program instructions for clustering wavefront signals in an electrophysiological map of a cardiac tissue. The program instructions cause a computer to execute the steps of receiving an electrophysiological map of the cardiac tissue, displaying propagation of the wavefront signals as a plurality of velocity vectors, discretizing the received electrophysiological map into a plurality of sections, clustering the velocity vectors into at least one group within each section based on predefined criteria, generating a trend line representative of each group of clustered velocity vectors within each section in the electrophysiological map, and displaying the trend lines in the electrophysiological map on a display.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Systems, methods, apparatuses, and programs for clustering wavefront signals for simplification in electrophysiological (EP) maps are disclosed herein.

Treatments for cardiac conditions such as cardiac arrhythmia often require obtaining a detailed mapping of cardiac tissue, chambers, veins, arteries and/or electrical pathways. For example, a prerequisite for performing a successful catheter ablation requires the location of the cardiac arrhythmia to be accurately identified in the heart chamber. Such locating may be done via an electrophysiological investigation during which electrical potentials are detected with a mapping catheter introduced into the heart chamber. This electrophysiological investigation, often referred to as an EP mapping, provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time Mapping of cardiac areas such as cardiac regions, tissue, veins, arteries and/or electrical pathways of the heart may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping may include mapping based on one or more modalities such as, but not limited to local activation time (LAT), an electrical activity, a topology, a bipolar mapping, a dominant frequency, or an impedance. Data corresponding to multiple modalities may be captured using a catheter inserted into a patient's body and may be provided for rendering at the same time or at different times based on corresponding settings and/or preferences of a medical professional.

In an embodiment, EP cardiac mapping may be implemented by sensing an electrical property of heart tissue, for example, local activation time (LAT), as a function of the precise location within the heart. The corresponding data may be acquired with one or more catheters that are advanced into the heart using catheters that have electrical and location sensors in their distal tips. As an example, location and electrical activity may be measured at 100's or 1000's of cardiac points or sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Figure 1:
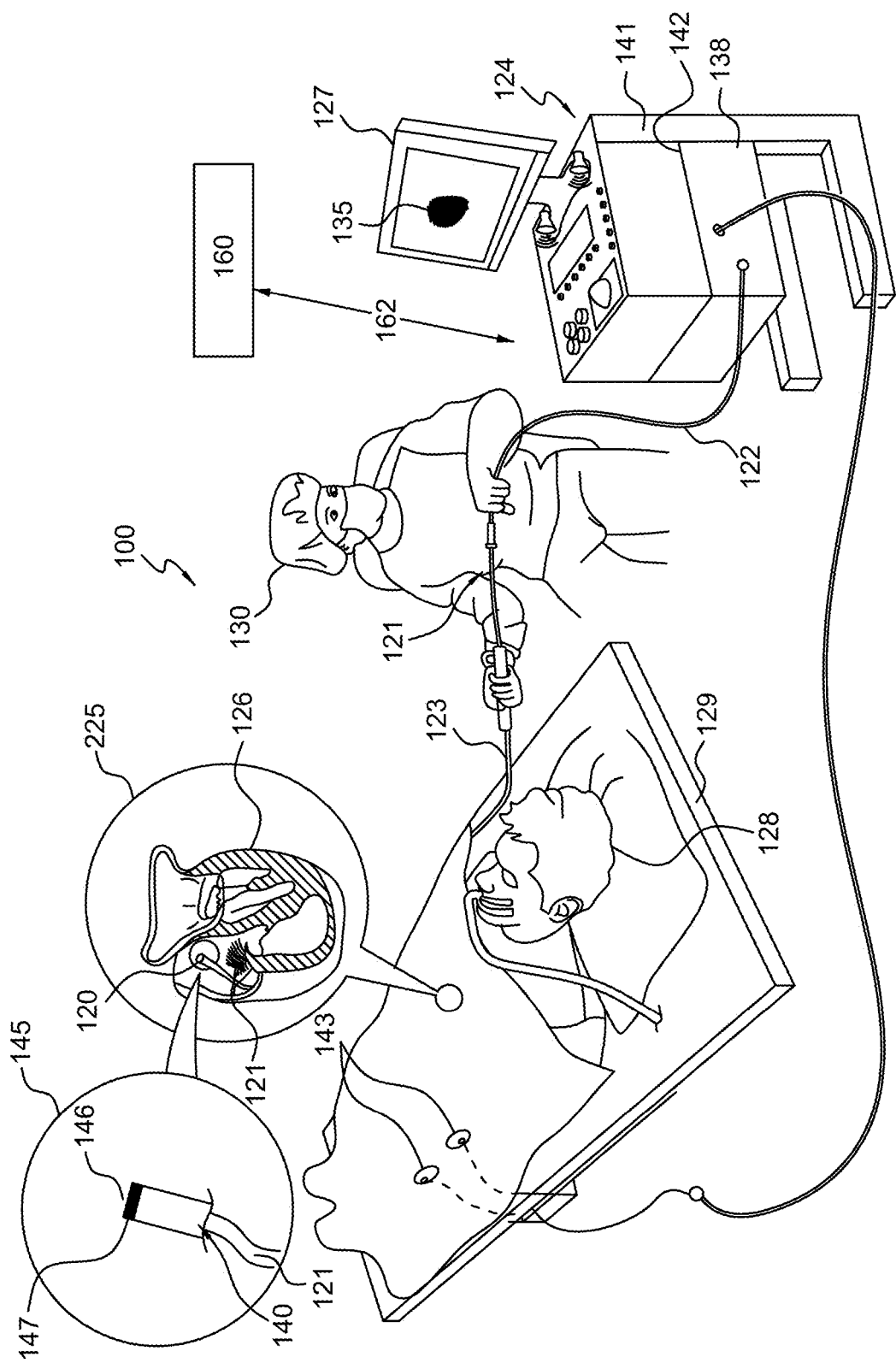
FIG. 1 shows an exemplary electrophysiological (EP) mapping system in which one or more features of the disclosed subject matter can be implemented in accordance with disclosed embodiments of the present application.

In an embodiment, electrical activity at a point in the heart may be measured by advancing a catheter containing an electrical sensor at or near its distal tip to that point in the heart, contacting the tissue with the sensor and acquiring data at that point. Such catheters containing electrical and/or sensors may also be used to determine the velocity and direction of cardiac wavefront signals at measured points on the cardiac surface. EP maps depicting such motion characteristics may be constructed when the wavefront velocity and direction information is sampled at a sufficient number of points in the heart. According to other examples, body patches and/or body surface electrodes may be positioned on or proximate to a patient's body. A catheter with one or more electrodes may be positioned within the patient's body (e.g., within the patient's heart) and the position of the catheter may be determined by a system based on signals transmitted and received between the one or more electrodes of the catheter and the body patches and/or body surface electrodes. Additionally, the catheter electrodes may sense biometric data (e.g., LAT values) from within the body of the patient (e.g., within the heart). The biometric data may be associated with the determined position of the catheter such that a rendering of the patient's body part (e.g., heart) may be displayed and may show the biometric data overlaid on a shape of the body part, as determined by the position of the catheter. FIG. 1 is a diagram of an exemplary EP mapping system 100 in which one or more features of the disclosed subject matter can be implemented. EP mapping system 100 may include one or more biometric devices 120, such as a catheter 140 (illustrated in inset 145). For example, and without limitation, the biometric device 120 may be configured to obtain biometric data, such as imaging signals, electronic signals, wavefront propagation information. One of skill in the art will recognize that catheter 140 can be any shape and can include one or more elements (e.g., electrodes or sensors) used to implement the embodiments disclosed herein. EP mapping system 100 includes a probe 121, having one or more shafts 122 that may be navigated by a physician 130 into a body part, such as heart 126, of a patient 128 lying on a table 129. According to exemplary embodiments, multiple probes 121 may be provided, however, for purposes of conciseness, a single probe 121 is described in this example, but it will be understood that probe 121 may represent multiple probes. As shown in FIG. 1, physician 130 may insert probe 121 through a sheath 123, while manipulating shaft 122 at the distal end of probe 121 using a manipulator near the proximal end of the invasive device and/or deflection from the sheath 123. As shown in an inset 225, a biometric device 120 may be fitted at the distal end of probe 121. Biometric device 120 may be inserted through sheath 123 to obtain biometric data of heart 126. For example, inset 145 shows catheter 140 in an enlarged view, inside a cardiac chamber of heart 126. As shown, catheter 140 may include a tip 146 with at least one measuring device 147 for measuring biometric or physiological information of the heart 126.

According to embodiments disclosed herein, biometric information may also include one or more of LATs, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 1, the probe 121 may be connected to a console 124. Console 124 may include a processor 141, such as a general-purpose computer, with suitable front end and interface circuits 138 for transmitting and receiving signals to and from biometric device 120, as well as for controlling the other components of EP mapping system 100. In some embodiments, processor 141 may be further configured to receive biometric data, such as electrical activity, and determine if a given tissue area conducts electricity. According to an embodiment, the processor may be external to the console 124 and may be located, for example, in the catheter, in an external device, in a mobile device, in a remote location, in a cloud-based device, or may be a standalone processor.

As noted above, processor 141 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 1 may be modified to implement the embodiments disclosed herein. The disclosed embodiments may similarly be applied using other system components and settings. Additionally, EP mapping system 100 may include additional components, such as elements for sensing electrical activity, wired or wireless connectors, processing and display devices, or the like.

According to an embodiment, a display 127 connected to a processor (e.g., processor 141) may be located at a remote location such as a separate hospital or in separate healthcare provider networks. Additionally, the EP mapping system 100 may be part of a surgical system that is configured to obtain anatomical and electrical measurements of a patient's organ, such as a heart, and performing a cardiac ablation procedure. An example of such a surgical system is the CARTO® System sold by Biosense Webster.

The EP mapping system 100 may also, and optionally, obtain biometric data such as anatomical measurements of the patient's heart using ultrasound, computed tomography (CT), magnetic resonance imaging (MRI) or other medical imaging techniques known in the art. The EP mapping system 100 may obtain electrical measurements using catheters 140, body surface electrodes 143 or other sensors that measure electrical properties of the heart. The biometric data including anatomical and electrical measurements may then be stored in a memory 142 of the EP mapping system 100, as shown in FIG. 1. The biometric data may be transmitted to the processor 141 from the memory 142. Alternatively, or in addition, the biometric data may be transmitted to a server 160, which may be local or remote, using a network 162. Server 160 may include a processing device for additional review, analysis, and processing of the biometric data.

Network 162 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the EP mapping system 100 and the server 160. The network 162 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 162.

In some instances, the server 160 may be implemented as a physical server. In other instances, server 162 may be implemented as a virtual server a public cloud computing provider (e.g., Amazon Web Services (AWS)®).

Processor 141 may include real-time noise reduction circuitry typically configured as a field programmable gate array (FPGA), followed by an analog-to-digital (A/D) ECG (electrocardiograph) or EMG (electromyogram) signal conversion integrated circuit. The processor 141 may pass the signal from an A/D ECG or EMG circuit to another processor and/or can be programmed to perform one or more functions disclosed herein.

Control console 124 may also include an input/output (I/O) communications interface that enables the control console to transfer signals from, and/or transfer signals to biometric device 120.

During or after a procedure, processor 141 may facilitate the presentation of a body part rendering 135 to physician 130 on a display 127, and store data representing the body part rendering 135 in a memory 142. Memory 142 may comprise any suitable volatile and/or non-volatile memory, such as random-access memory or a hard disk drive. In some embodiments, medical professional 130 may be able to manipulate a body part rendering 135 using one or more input devices such as a touch pad, a mouse, a keyboard, a gesture recognition apparatus, or the like. For example, an input device may be used to change the position of catheter 140 such that rendering 135 is updated. In alternative embodiments, display 127 may include a touchscreen that can be configured to accept inputs from medical professional 130, in addition to presenting a body part rendering 135

Figure 2:
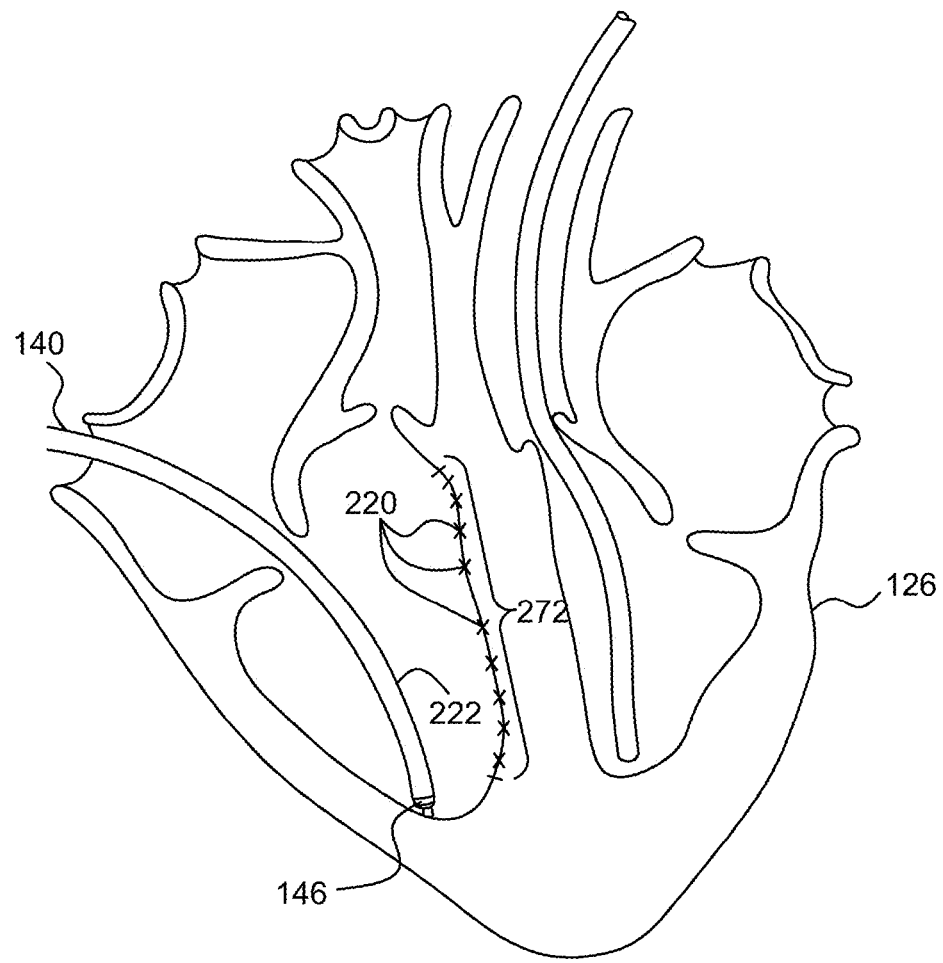
FIG. 2 illustrates a catheter within a heart of a patient in accordance with a disclosed embodiment of the present application.

FIG. 2 illustrates an exemplary embodiment of distal end 222 of catheter 140 positioned within a heart 126 of patient 128, in accordance with an embodiment of the present application. Catheter 140 is inserted into heart 126 and tip 146 is brought into contact with a plurality of locations, such as locations 220 on an inner surface 272 of heart 126. At each of the plurality of locations, the coordinates of tip 146 are determined by measuring device 147. The determined coordinates and, optionally, physiological information, form a local data point.

In an embodiment, an example of a physiological parameter of the heart 126, that is measured using measuring device 147 of catheter 140, is the local activation time (LAT) of the heart tissue. This time is determined by referring the time of a feature of the signal (specifically, a voltage) measured by functional measuring device 147 at each sampled point, for example, the time in the cardiac cycle at which that signal first exceeds a certain threshold, to the time within the cardiac cycle of a fiducial feature of the ECG signal, as measured, for example, using an ECG monitor. A propagation velocity of the LAT signal, i.e., a conduction velocity of the heart tissue, is obtained by assigning a velocity vector to each sampled point, based on the measured LAT signal values utilizing methods that are known to one of skill in the art, such as that described in U.S. Pat. No. 6,301,496, which is incorporated by reference as if fully set forth. The conduction velocity vectors can be superimposed as arrows on a 3D model of the heart or heart segment in an EP mapping system, such as system 100. In an embodiment, the direction of the arrows represent the direction of propagation of the wavefront signal and the length of the arrows represents the velocity of propagation of the wavefront. These arrows provide a visual display of conduction velocity of the heart tissue to enable a physician to assess and determine a method of treatment for diseased cardiac tissue.

Figure 3:
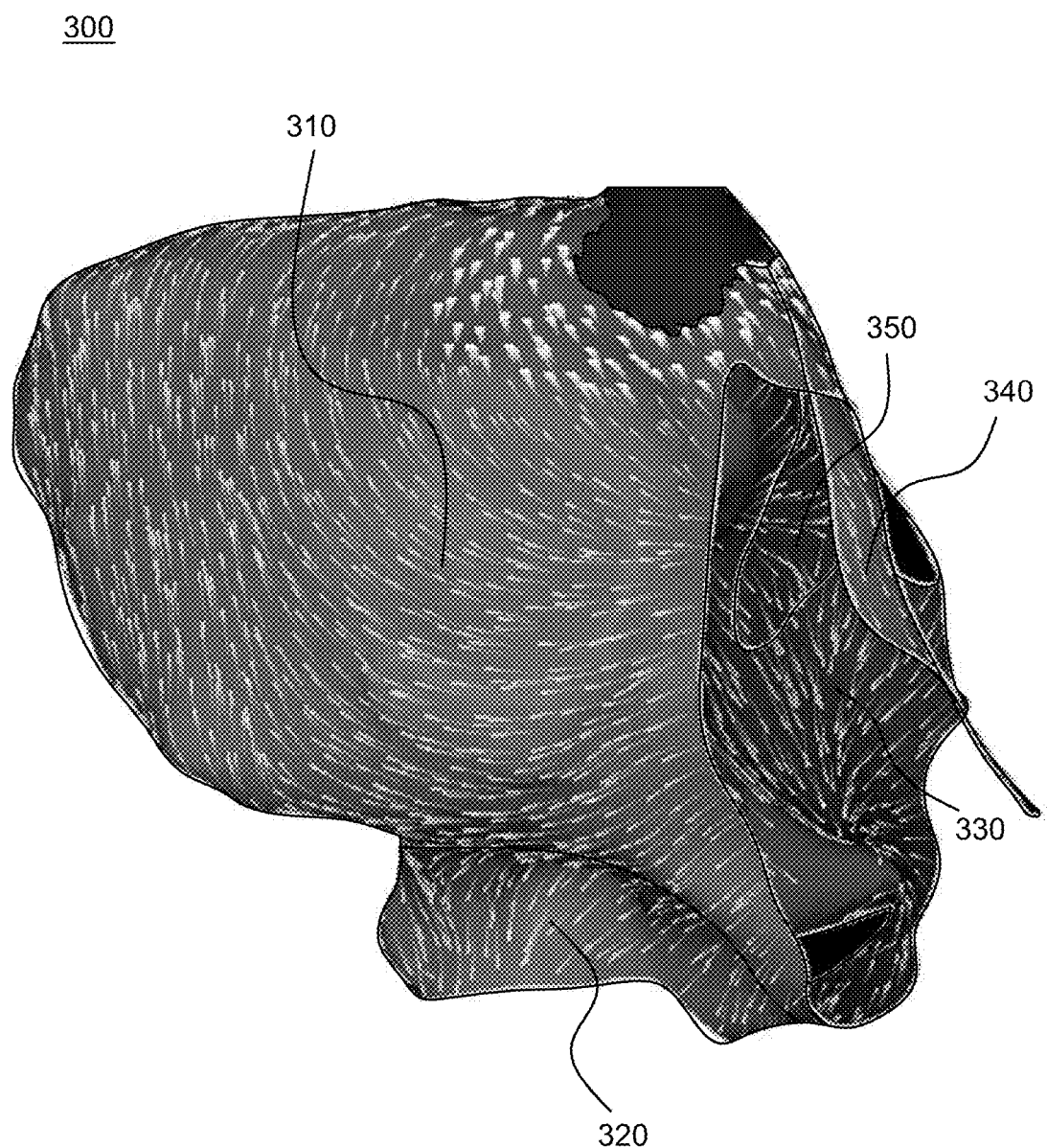
FIG. 3 illustrates a view of a 3D EP map illustrating local activation times (LATs) associated with a cardiac tissue with conduction velocity vectors superimposed as arrows.

In conventional 3D EP mapping systems, the conduction velocity vectors superimposed as arrows on a 3D model of the heart or heart segment can be difficult to interpret as they typically present 100's or 1000's of velocity vectors. FIG. 3 is an exemplary embodiment of a 3D EP map illustrating local activation times (LATs) associated with a cardiac tissue. The cardiac tissue can be, for example and without limitation, a cardiac chamber such as an atrial chamber or a left or right atrium. The LAT is an indication of the flow of electrical activity through walls of the heart. In particular, FIG. 3 illustrates conduction velocity vectors superimposed as arrows. As shown in FIG. 3, the number of conduction velocity vectors is large, redundant, and difficult to follow, particularly for an inexperienced physician.

Figure 4:
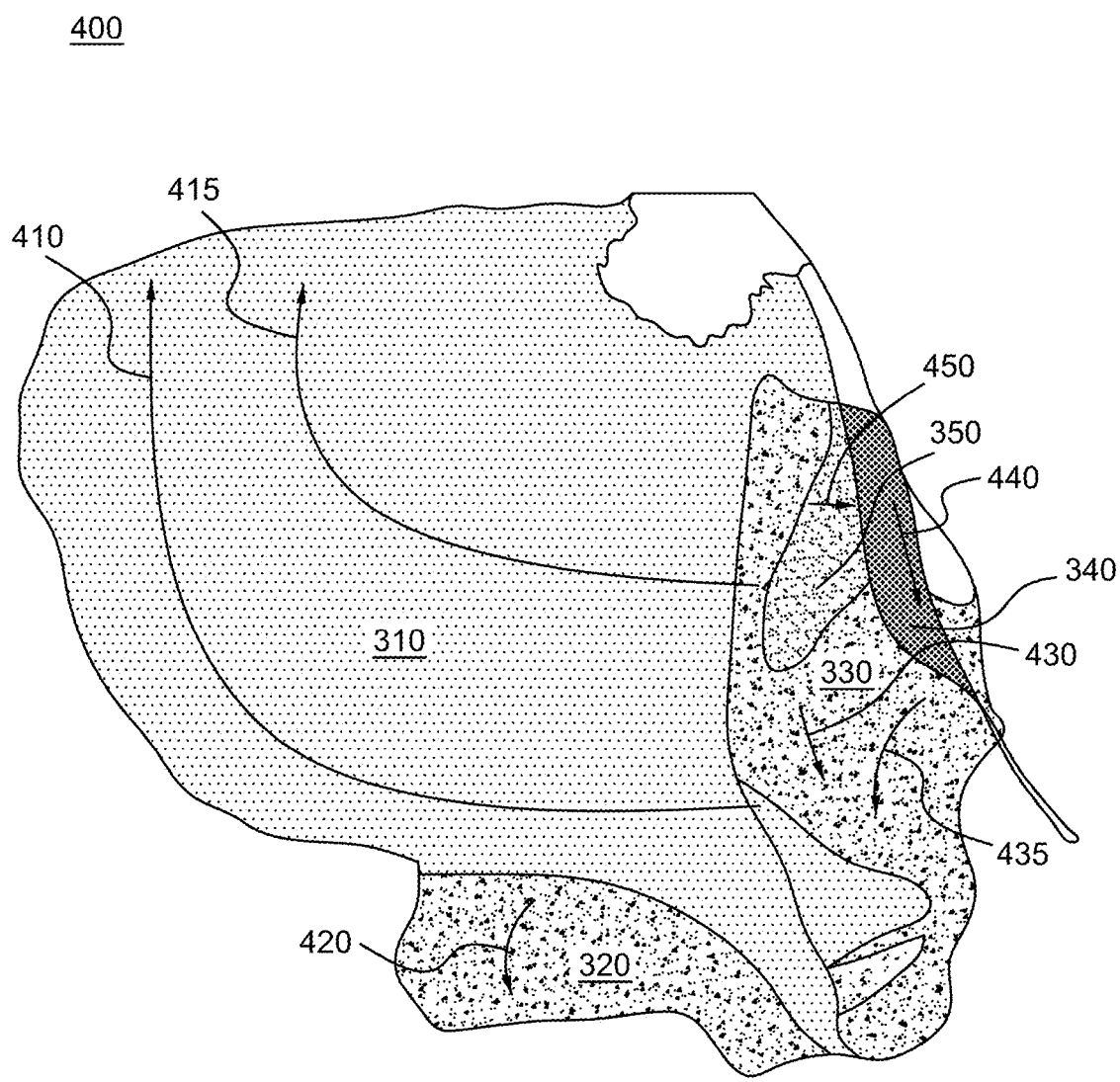
FIG. 4 illustrates an exemplary 3D EP map of a cardiac tissue with multiple trend lines conveying the propagation of wavefront signals in accordance with a disclosed embodiment of the present application.
Figure 5:
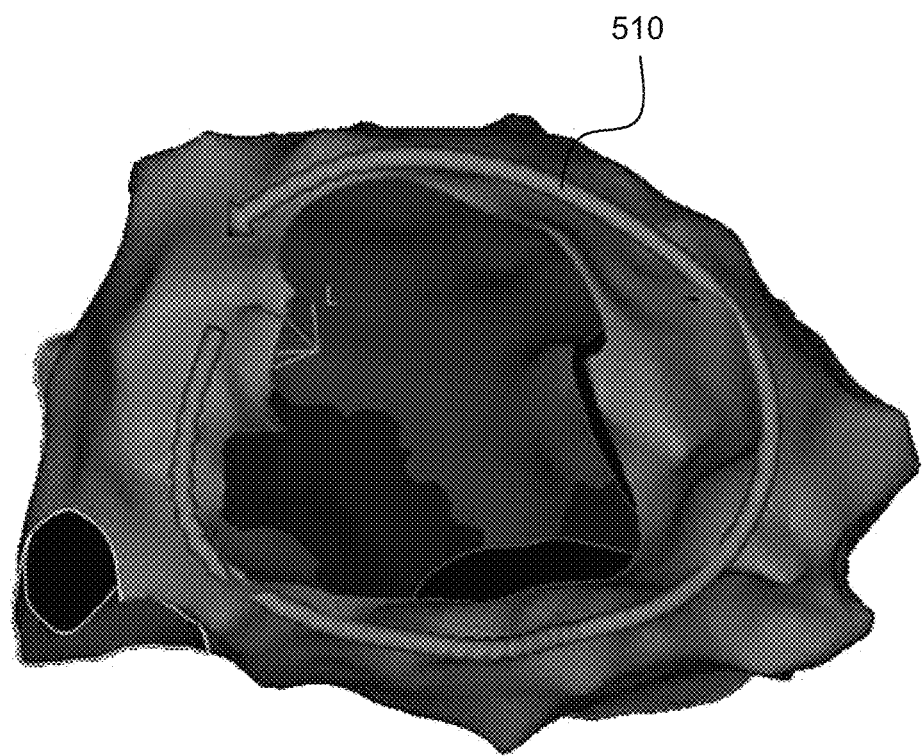
FIG. 5 illustrates an exemplary 3D EP map of a cardiac tissue showing a single trend line conveying the propagation of wavefront signals over an entire cycle length in accordance with a disclosed embodiment of the present application.

In an embodiment, the subject matter of the present application is directed to simplifying 3D EP cardiac maps by reducing the volume of information presented. More particularly, the subject matter of the present application is directed to utilizing a clustering algorithm to generate a trend line, instead of individual velocity vectors, to show wavefront propagation in cardiac tissue. The output of the clustering algorithm conveys similar information as conventional LAT maps, but with reduced graphical information as a result of clustering multiple conduction velocity vectors into one or a few trend lines. For example, as illustrated in FIG. 4, discussed in more detail herein, multiple trend lines (410, 415, 420, 430, 435, 440, 450) can be superimposed on an EP map 400, or, as illustrated in FIG. 5, discussed in more detail herein, a single trend line 510 can be superimposed on an EP map 500 to show propagation of wavefront signals.

Figure 6:
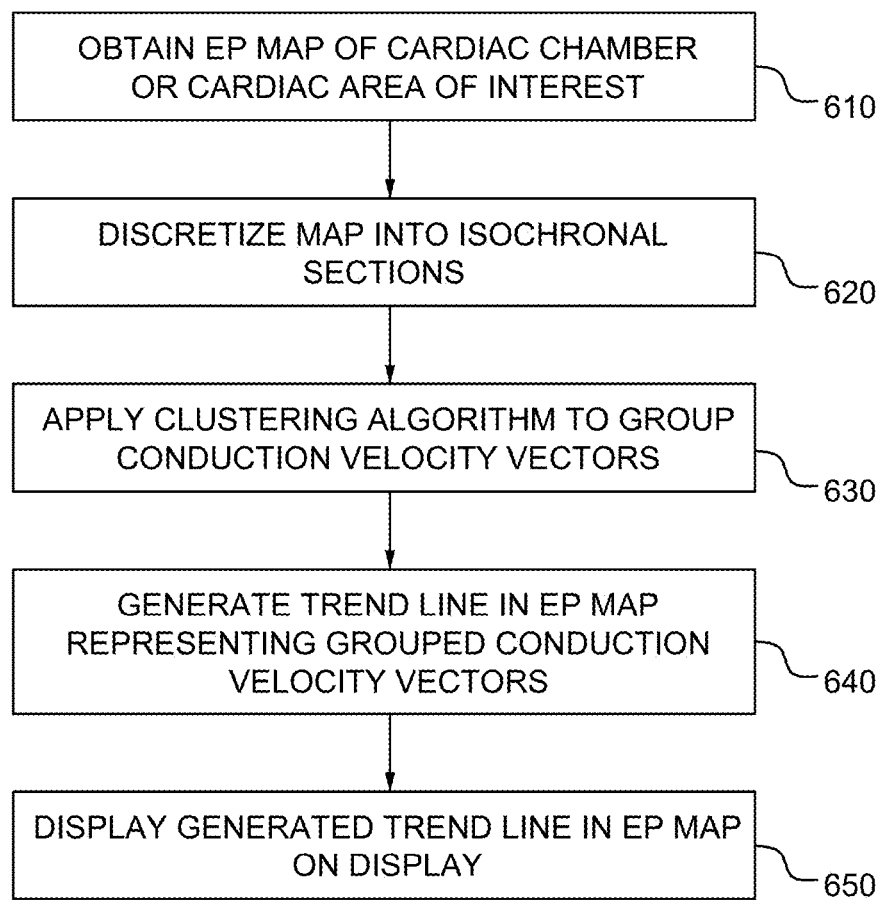
FIG. 6 is a flow diagram illustrating an exemplary embodiment of a process for generating trend lines representing wavefront propagation in an EP map of a cardiac

FIG. 6 is an exemplary embodiment of a process 600 for generating trend lines representing wavefront propagation in an EP map of a cardiac tissue utilizing the clustering algorithm of the present application.

At step 610, a processing device, such as processor 141 and memory 142 associated with EP mapping system 100 (FIG. 1), preferably receives and stores an EP map of a cardiac chamber or cardiac area of interest. The processing device can be at the same location as the EP mapping system, or can be located remotely from the EP mapping system or stored in the cloud. In an embodiment, the EP map is a 3D EP map illustrating LATs associated with a cardiac tissue, such as, for example and without limitation, EP map 300 shown in FIG. 3 illustrating a large volume of conduction velocity vectors.

At step 620, the processing device preferably discretizes the EP map into isochronal sections. For example, FIG. 3 illustrates isochronal sections 310, 320, 330, 340, 350 generated by discretization of the EP map coloring. In an embodiment, the coloring is interpolated as a representation of local activation time (LAT) for each point on the map, where each color is mapped to a number, for example and without limitation, such as a number representing a time or an amount of time. The isochronal sections 310, 320, 330, 340, 350 are generated by segmenting the coloring or time points on the EP map into several time segments, where each common time segment refers to one isochronal segment.

In an embodiment, the coloring and the velocity vectors can be determined as a result of the "coherent" algorithm currently in the above noted CARTO® System. This System may be modified by those skilled in the art to embody the principles described herein. One of skill in the art will recognize that other systems, methods, and algorithms that compute LAT (wave time) and direction (velocity vectors) for each point in an EP map can be utilized in accordance with the subject matter of the present application, such as those disclosed in commonly assigned, U.S. Pat. No. 10,282,888 and 10,674,929, which are incorporated by reference as if fully set forth. For example, the coloring can be interpolated using a Laplacian operator over given time points on the EP map, and the velocity vectors can be derived by computing the discrete gradient over the time function.

While five (5) isochronal sections are illustrated in FIG. 3, one of ordinary skill in the art will recognize that any number of isochronal sections can be generated without departing from the subject matter of the present application. While the term "coloring" is used herein with reference to the EP map, one of skill in the art will recognize that "coloring" can include variations based on colors, brightness, or grey scale range, indicative of the different times associated with each isochronal section, within the scope of the present application.

At step 630, the processing device preferably applies a clustering algorithm in accordance with the present application to cluster or group conduction velocity vectors from multiple points within an isochronal section. For example and without limitation, the clustering algorithm can group conduction velocity vectors based on predefined criteria, such as a position within a predefined proximity, a common direction, or a common propagation velocity. In an embodiment the predefined criteria can be set by a user, such as a physician, or can be determined as a result of a machine learning algorithm employed by the processing device.

At step 640, the processing device preferably generates at least one trend line in each isochronal section in the EP map representative of the grouped conduction velocity vectors. FIG. 4 illustrates an exemplary embodiment of a 3D EP map 400 of a cardiac structure showing trend lines 410, 415, 420, 430, 435, 440, 450 representative of the grouped velocity vectors. For example:

trend lines 410 and 415 are representative of grouped velocity vectors in isochronal section 310;

trend line 420 is representative of grouped velocity vectors in isochronal section 320;

trend lines 430 and 435 are representative of grouped velocity vectors in isochronal section 330;

trend line 440 is representative of grouped velocity vectors in isochronal section 340; and trend line 450 is representative of grouped velocity vectors in isochronal section 350.

As shown in FIG. 4, for example, the trend lines 410, 415, 420, 430, 435, 440, 450 can be visually illustrated by arrows. However, one of skill in the art will readily understand that the trend lines are not limited to arrows, and that other graphical indicators, such as lines, dots, x's, color patterns, etc., can be used to visually illustrate the trend lines.

The number of trend lines generated in each isochronal section can be based on the predetermined criteria. For example, while 2 trends lines 410, 415 are generated in isochronal 310 in FIG. 4, the clustering algorithm can be programmed to generate a single trend line in each isochronal or 2 or more trend lines in each isochronal based on the predefined criteria.

FIG. 5 illustrates an exemplary embodiment of a 3D EP map 500 of a cardiac structure showing a single trend line 510 representative of the grouped velocity vectors in an isochronal section generated by the clustering algorithm described herein. As show in FIG. 5, the single trend line 510 can have a circular pattern representative of propagation of a wavefront signal over an entire cardiac cycle length.

At step 650, the trend lines generated in the EP map can be displayed on a display, such as display 127 (FIG. 1). Alternatively, the trend lines generated in the EP map can be displayed on a remote display, such as a display associated with server 160. In an embodiment, the trend lines are displayed without the conduction velocity vectors, such as shown in FIG. 4. Alternatively, the trend lines can be overlaid on the conduction velocity vectors and visibly distinguished, such as by different greyscale, color or pattern.

The subject matter disclosed herein for clustering wavefront information for presentation in an EP map provides for a more simplified visualization of propagation of electromagnetic wavefront signals moving through a cardiac structure compared to displays in conventional EP maps. This accomplished by reducing the clutter caused by the 100's or 1000's of velocity vectors presented in conventional EP maps and providing a condensed visualization of a limited number of trend lines representing groupings of conduction velocity vectors. The trend line information conveys similar information as conventional conduction velocity vectors, but is presented in a graphical display that easy to understand, particularly for new physicians.

The isochronal segment generation described herein reduces the complexity of determining propagation of a wavefront signal. As described herein, a trend line is generated in each isochronal region representative of the wave front propagation. As a result, the greater the number of isochronal regions in a given space, the more accurate the generated trend line will be in the EP map.

While the description above has been generally directed to having a processing device analyze local activation times of cardiac tissue, it will be understood that the subject matter of the present application is not limited as such and may be applied to other physiological parameters associated with other body organs. For example, rather than operating with times, the processing device may be configured to operate with and cluster voltages traversing an organ. As another example, there is heat flow during ablation of an organ, and the heat flow through the organ may manifest itself as temperature changes of the organ. The processing device may be configured to analyze and cluster measured temperatures of the organ. Those having ordinary skill in the art will be able to identify other physiological parameters that the processing device is applicable to within the scope of the present application.

It should be understood that many variations are possible based on the disclosure herein. Although features and elements are described above in particular combinations, each feature or element can be used alone without the other features and elements or in various combinations with or without other features and elements. Similarly, although process steps are described above in a particular order, the steps can be performed in other desirable orders.

The methods, processes and/or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

Certain terminology is used in the description herein for convenience only and is not limiting. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Further exemplary embodiments herein may be formed by supplementing an embodiment with one or more element from any one or more other embodiment herein, and/or substituting one or more element from one embodiment with one or more element from one or more other embodiment herein.

It is understood, therefore, that the disclosed subject matter is not limited to the particular embodiments disclosed, but is intended to cover all modifications which are within the spirit and scope of the invention as defined by the appended claims; the above description; and/or shown in the attached drawings.

What is claimed is:

1. A method for clustering wavefront signals in an electrophysiological map of a cardiac tissue, comprising:
   providing a processor configured to receive an electrophysiological map of the cardiac tissue, the electrophysiological map including a plurality of wavefront signals;
   displaying propagation of the plurality of wavefront signals as a plurality of velocity vectors;
   discretizing the received electrophysiological map into a plurality of isochronal sections;
   clustering the plurality of velocity vectors into at least one group within each isochronal section based on predefined criteria; and
   generating a trend line representative of each group of clustered velocity vectors within each isochronal section in the electrophysiological map.

2. The method of claim 1, wherein the cardiac tissue is an atrial chamber.

3. The method of claim 1, wherein the received electrophysiological map is a 3D map of local activation times associated with the cardiac tissue.

4. The method of claim 1, wherein the electrophysiological map is discretized based on the direction of the plurality of velocity vectors.

5. The method of claim 1, wherein clustering further comprises applying a clustering algorithm to group the plurality of velocity vectors.

6. The method of claim 1, wherein the predefined criteria for clustering the plurality of velocity vectors comprises at least one of a predefined proximity, a common direction, or a common propagation velocity.

7. The method of claim 1, further comprising displaying the trend lines as arrows in a 3D electrophysiological map on a display.

8. The method of claim 1, wherein the processor is a component of an electrophysiological mapping system.

9. The method of claim 1, wherein the electrophysiological map is generated by an electrophysiological mapping system.

10. A system for clustering wavefront signals in an electrophysiological map of a cardiac tissue, comprising:
    a processor comprising a memory configured to:
       receive an electrophysiological map of the cardiac tissue displaying propagation of the wavefront signals as a plurality of velocity vectors;
       discretize the received electrophysiological map into a plurality of isochronal sections;
       cluster the plurality of velocity vectors into at least one group within each isochronal section based on predefined criteria; and generate a trend line representative of each group of clustered velocity vectors within each isochronal section in the electrophysiological map.

11. The system of claim 10, wherein the cardiac tissue is an atrial chamber.

12. The system of claim 10, wherein the received electrophysiological map is a 3D map of local activation times associated with the cardiac tissue.

13. The system of claim 10, wherein the electrophysiological map is discretized based on the direction of the plurality of velocity vectors.

14. The system of claim 10, wherein the processor is further configured to apply a clustering algorithm to cluster the plurality of velocity vectors.

15. The system of claim 10, wherein the predefined criteria for clustering the plurality of velocity vectors comprises at least one of a predefined proximity, a common direction, or a common propagation velocity.

16. The system of claim 10, wherein
the electrophysiological map is a 3D electrophysiological map; and
the processor is further configured to display the trend lines as arrows in the 3D electrophysiological map on a display.

17. The system of claim 10, wherein the processor is a component of an electrophysiological mapping system.

18. A non-transitory computer readable recording medium storing program instructions for clustering wavefront signals in an electrophysiological map of a cardiac tissue by causing a computer to execute the steps of:

receiving an electrophysiological map of the cardiac tissue, the electrophysiological map including a plurality of wavefront signals;

displaying propagation of the plurality of wavefront signals as a plurality of velocity vectors;

discretizing the received electrophysiological map into a plurality of isochronal sections;

clustering the plurality of velocity vectors into at least one group within each isochronal section based on predefined criteria;

generating a trend line representative of each group of clustered velocity vectors within each isochronal section in the electrophysiological map; and displaying the trend lines in the electrophysiological map on a display.

* * * * *

UNITED STATES PATENT AND TRADEMARK OFFICE
CERTIFICATE OF CORRECTION

PATENT NO. : 11,432,755 B2
APPLICATION NO. : 17/027252
DATED : September 6, 2022
INVENTOR(S) : Assaf Cohen et al.

Page 1 of 1

It is certified that error appears in the above-identified patent and that said Letters Patent is hereby corrected as shown below:

On the Title Page

On Page 2, in Item (56), in Column 1, Line 1, delete "et al," and insert -- et al., --, therefor.

In the Specification

In Column 1, Line 64, delete "one an" and insert -- one --, therefor.
In Column 3, Line 24, delete "time" and insert -- time. --, therefor.
In Column 6, Line 2, delete "server 162" and insert -- server 160 --, therefor.
In Column 6, Line 32, delete "135" and insert -- 135. --, therefor.
In Column 6, Line 46, delete "referring the" and insert -- referring to the --, therefor.
In Column 8, Line 61, delete "show" and insert -- shown --, therefor.
In Column 9, Line 12, delete "accomplished" and insert -- is accomplished --, therefor.

In the Claims

In Column 11, Line 18, in Claim 16, delete "wherein" and insert -- wherein: --, therefor.

Signed and Sealed this
Fifth Day of September, 2023

Katherine Kelly Vidal
*Director of the United States Patent and Trademark Office*